(12) United States Patent
Lin

(10) Patent No.: US 6,896,677 B1
(45) Date of Patent: May 24, 2005

(54) ROTARY DEVICE FOR RETRIEVING SPINAL COLUMN UNDER TREATMENT

(75) Inventor: Chih-I Lin, Taipei (TW)

(73) Assignees: A-Spine Holding Group Corp., Tortola (VG); A-Spine Asia Co., Ltd., Taipei (TW)

( * ) Notice: Subject to any disclaimer, the term of this patent is extended or adjusted under 35 U.S.C. 154(b) by 0 days.

(21) Appl. No.: 10/862,421

(22) Filed: Jun. 8, 2004

(30) Foreign Application Priority Data

Dec. 11, 2003 (TW) .............................. 92135098 A

(51) Int. Cl.⁷ ............................................ A61B 17/70
(52) U.S. Cl. ...................................................... 606/61
(58) Field of Search .............................. 606/60, 61, 72, 606/73; 623/17.11

(56) References Cited

U.S. PATENT DOCUMENTS

| | | | | |
|---|---|---|---|---|
| 5,217,497 A | * | 6/1993 | Mehdian ....................... 623/17 |
| 5,443,467 A | * | 8/1995 | Biedermann et al. ......... 606/65 |
| 5,496,321 A | * | 3/1996 | Puno et al. .................... 606/61 |
| 5,683,390 A | * | 11/1997 | Metz-Stavenhagen et al. ........ 606/61 |
| 5,683,394 A | * | 11/1997 | Rinner ......................... 606/61 |
| 6,090,111 A | * | 7/2000 | Nichols ........................ 606/61 |
| 6,280,442 B1 | * | 8/2001 | Barker et al. ................. 606/60 |
| 6,471,705 B1 | * | 10/2002 | Biedermann et al. ......... 606/61 |
| 6,488,681 B2 | * | 12/2002 | Martin et al. ................. 606/61 |
| 6,565,565 B1 | * | 5/2003 | Yuan et al. ................... 606/61 |
| 6,565,567 B1 | * | 5/2003 | Haider ......................... 606/61 |
| 6,652,526 B1 | * | 11/2003 | Arafiles ....................... 606/61 |
| 2004/0138660 A1 | * | 7/2004 | Serhan ......................... 606/61 |

* cited by examiner

Primary Examiner—Eduardo C. Robert
Assistant Examiner—David Comstock
(74) Attorney, Agent, or Firm—Bacon & Thomas PLLC

(57) ABSTRACT

A vertebral retrieval device includes a retrieval rod which is gripped firmly in a receiving slot of a fixation seat between two grooves of a pressing element and a C-shaped ring. The C-shaped ring rests on a spherical head fastening screw, a spherical head of which is received in the fixation seat and a shank of which is protruding from a through hole provided in a bottom of the fixation seat. The pressing element is pressed against the retrieval rod by a pressing screw, which is threaded into a threaded hole formed in a fixation element mounted in the receiving slot of the fixation seat.

5 Claims, 4 Drawing Sheets

ROTARY DEVICE FOR RETRIEVING SPINAL COLUMN UNDER TREATMENT

FIELD OF THE INVENTION

The present invention relates generally to a spinal surgical care device, and more particularly to a rotary device for retrieving spine column under treatment.

BACKGROUND OF THE INVENTION

The inventor of this application in U.S. patent published No. 20030187434 A1 discloses a vertebral fixation device comprising a fixation seat, a fixation block, and a fastening bolt. The fixation seat is provided with a receiving slot for receiving a vertebral fixation rod. The fixation block is engaged with the fixation seat such that the vertebral fixation rod is pressed by the fixation block, and that two retaining edges of the fixation block are retained in two retaining recesses of the fixation seat. The fastening bolt is engaged with a threaded through hole of said fixation block such that one end of the fastening bolt presses against the vertebral fixation rod. Although this design improves the conventional backbone-fixing devices, there are at least the following defects which call for further improvements: 1) the contact of the spherical head fastening screw and the fixation rod is restricted to a thin line; and 2) the fixation block has to be fabricated precisely to well fasten the fixation rod in the receiving slot of the fixation seats. For this reason, the fixation rod is susceptible to unintentional displacement in a spinal surgery in progress. Such a displacement of the back-retrieving rod often affects adversely the outcome of the spinal surgery. U.S. Pat. No. 6,565,565 B1 discloses a device for securing spinal rods, which is similar to that described in the US patent published No. 20030187434 A1 with the common drawbacks.

SUMMARY OF THE INVENTION

A primary objective of the present invention is to provide a rotary device for fixing spinal column under treatment without the drawbacks of the prior art.

A vertebral retrieval device constructed according to the present invention comprises:

- a retrieval rod which is used to retrieve spinal segments under treatment;
- a fixation seat provided with a receiving slot for receiving the retrieval rod, said receiving slot being provided on two opposite side walls with a retaining recess, and in a bottom with a through hole;
- a fastening screw is provided with a spherical head made integrally therewith, wherein said spherical head is rotatably received in said fixation seat when said fastening screw is inserted into said through hole of said fixation seat;
- a C-shaped ring provided with a concave down surface on one side, said C-shaped ring being able to be elastically deformed, received in said fixation seat and retained in said fixation seat by an expansion force resulting from said deformation, while said concave down surface resting on the spherical head of said fastening screw and another side of said C-shaped ring being adapted to receive said retrieval rod;
- a fixation assembly comprising a rotary fixation element provided with a threaded through hole, and two retaining edges opposite to each other; a pressing element having a projection at one side and a groove at another side; and a pressing screw having a round hole adapted to receive said projection of said pressing element, wherein said rotary fixation element is engaged with said fixation seat such that the two retaining edges are retained in said retaining recesses of said fixation seat, said pressing screw is threadably engaged in said threaded through hole of said rotary fixation element, and the pressing element is able to be pressed against said retrieval rod by threading said pressing screw, when the groove of said pressing element rests on said retrieval rod and said projection of said pressing element is received in said round hole of said pressing screw.

Preferably, said retaining recesses of said fixation seat are located in inner sides of the two side walls of said receiving slot; wherein said retaining edges of said rotary fixation element are located in outer edges of said rotary fixation element. More preferably, said retaining edges of said rotary fixation element are provided with an inclined plane having a higher outer side and a lower inner side; wherein said retaining recesses of said fixation seat are provided with an inclined plane having a higher outer side and a lower inner side, wherein said rotary fixation element is engaged with said fixation seat such that said inclined planes of said rotary fixation element and said fixation seat are in contact with each other, and thus the two side walls of said receiving slot of said fixation seat are further prevented from departing from each other.

Preferably, said C-shaped ring is provided with a groove on said another side thereof, and said groove of said C-shaped ring is adapted to receive said retrieval rod;

Preferably, a tool hole is provided in said pressing screw for facilitating the threadable engagement with said rotary fixation element.

Said C-shaped ring of the present invention is elastically retained in the fixation seat and is pressed against the spherical head of the fastening screw, creating more friction between the C-shaped ring and the fixation seat/the spherical head of the fastening screw, so that the fastening thereof is improved. The groove of the C-shaped ring further enhances the friction and the fastening effect.

The pressing screw of the present invention can be threaded to press the pressing element against the fixation rod, which presses the C-shaped ring, which presses the spherical head of the fastening screw, which presses the fastening seat, so that the retrieval rod is gripped firmly in the receiving slot of the fixation seat, and thus it is secured to the fastening screw which has be fastened to a pedicle of a vertebra in advance.

The features and the advantages of the present invention will be more readily understood upon a thoughtful deliberation of the following detailed description of the present invention with reference to the accompanying drawings.

DETAILED DESCRIPTION OF THE PREFERRED EMBODIMENT

Figure 1:
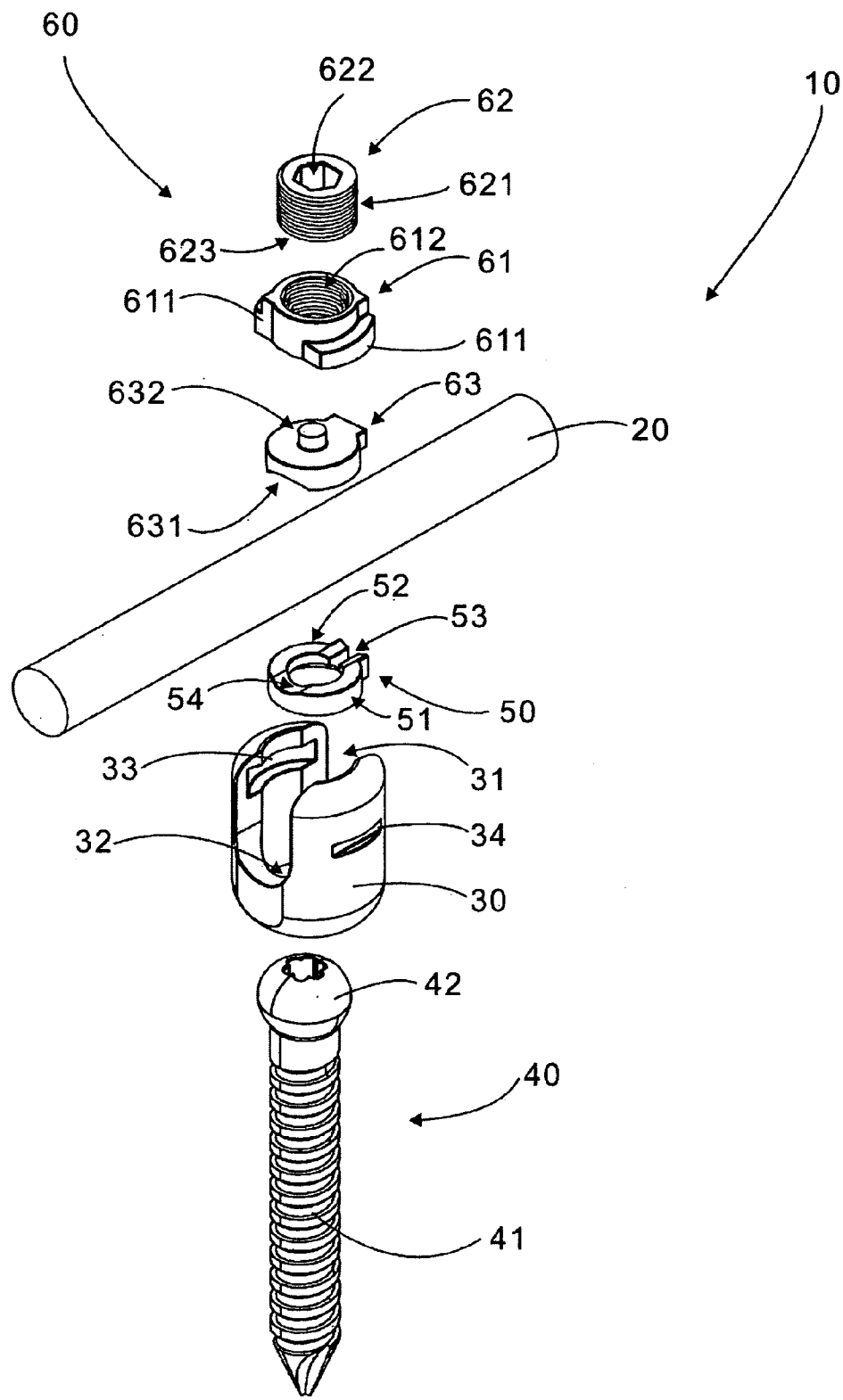
FIG. 1 shows an exploded view of a first preferred embodiment of the present invention.

As shown in FIGS. 1–4, a vertebral retrieval device 10 of the present invention comprises a retrieval rod 20, a fixation seat 30, a fastening screw 40, a C-shaped ring 50, and a fixation assembly 60.

The fixation seat 30 is provided with a U-shaped receiving slot 31 which has two retaining recesses 33 on the two inner walls, two clamping slots 34 on the outer walls, and a through hole 32 in the bottom.

Figure 2:
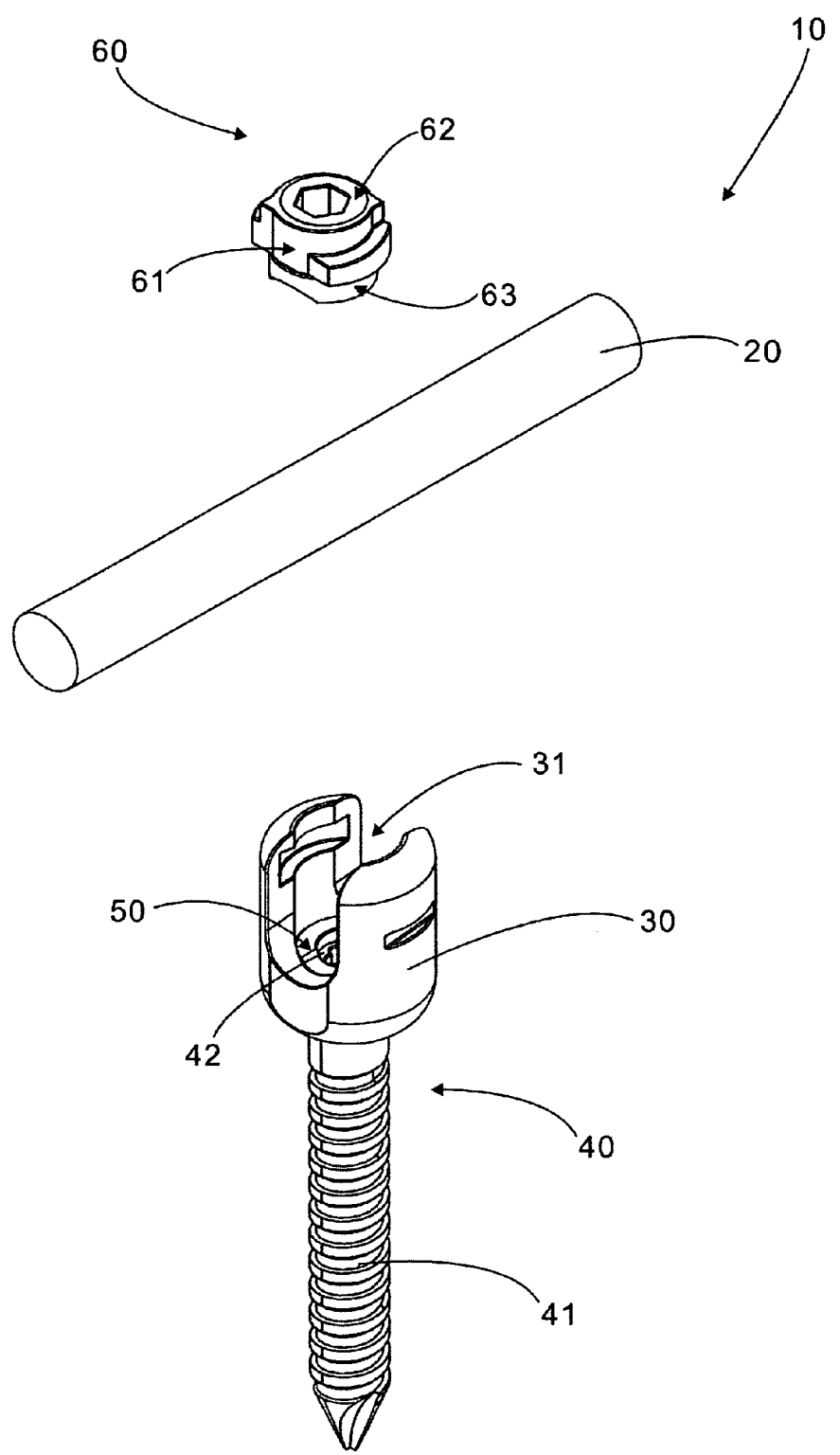
FIG. 2 shows a perspective view of the first preferred embodiment of the present invention shown in FIG. 1, when the fixation assembly 60 is assembled.
Figure 3:
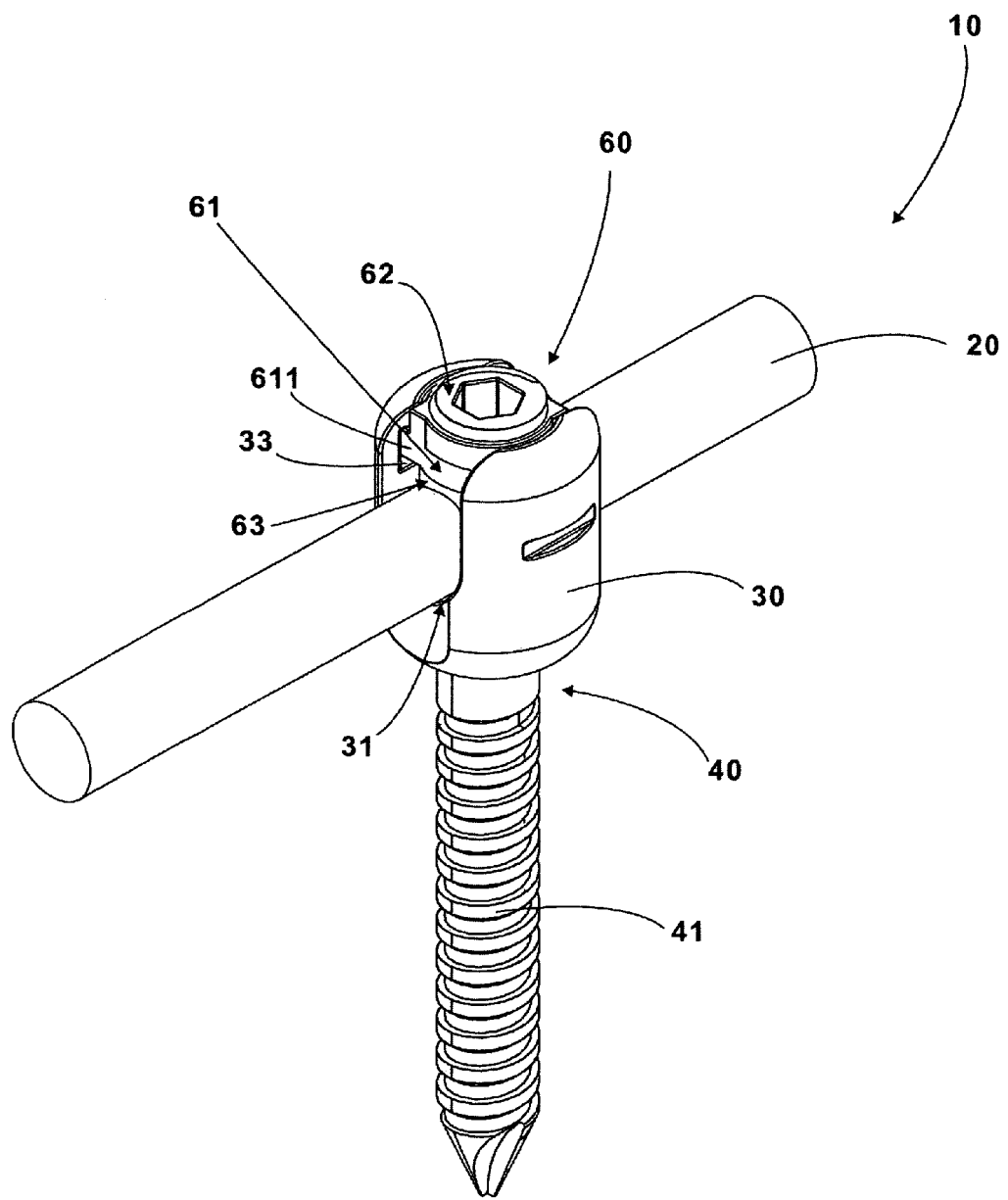
FIG. 3 shows a perspective view of the first preferred embodiment of the present invention shown in FIG. 1 at work.

The fixation assembly 60 has a rotary fixation element 61, a pressing screw 62 and a pressing element 63, which can be assemble before using, as shown in FIG. 2. The rotary fixation element 61 is provided with a threaded through hole 612 at the axial center, and two opposite retaining edges 611 protruding radially from the outer surface. The pressing element 63 has a cylindrical projection 632 at one side and a groove 631 at another side. The pressing screw 62 has a round hole 623 for receiving said projection 632 of said pressing element, and is threadably engaged in the threaded through hole 612 of the rotary fixation element 61.

The fastening screw is provided with a shank 41 and a spherical head 42 made integrally therewith, wherein said spherical head 42 is rotatably received in said fixation seat 30 when said shank 41 is protruding from said through hole 32 of said fixation seat. The shank 41 of the fastening screw 41 is then fastened to a pedicle of a vertebra under treatment (not shown in the drawings).

The C-shaped ring 50 is provided with a concave down surface 51 on one side, and a groove 54 adapted to receive said retrieval rod 20 on another side 52 thereof. Said C-shaped ring 50 can be elastically deformed due to an opening 53, received in said fixation seat 30 and retained in said fixation seat by an expansion force resulting from said deformation, while said concave down surface 51 resting on the spherical head 42 of said fastening screw 40.

The retrieval rod 20 is received in the receiving slot 31 of the fixation seat 30 and on the groove 54 of the C-shaped ring 50.

The fixation assembly 60 is rotated and connected to the fixation seat 30, wherein the rotary fixation element 61 is engaged with said fixation seat 30 such that the two retaining edges 611 are retained in said retaining recesses 33 of said fixation seat 30. The pressing element 63 is able to be pressed against said retrieval rod 20 by threading said pressing screw 62, wherein the groove 631 of said pressing element rests on said retrieval rod 62 and said projection 632 of said pressing element is received in said round hole 623 of said pressing screw. The pressing screw 62 is provided with a tool hole 622 for facilitating the threadable engagement with said rotary fixation element 61 and the pressing.

Figure 4:
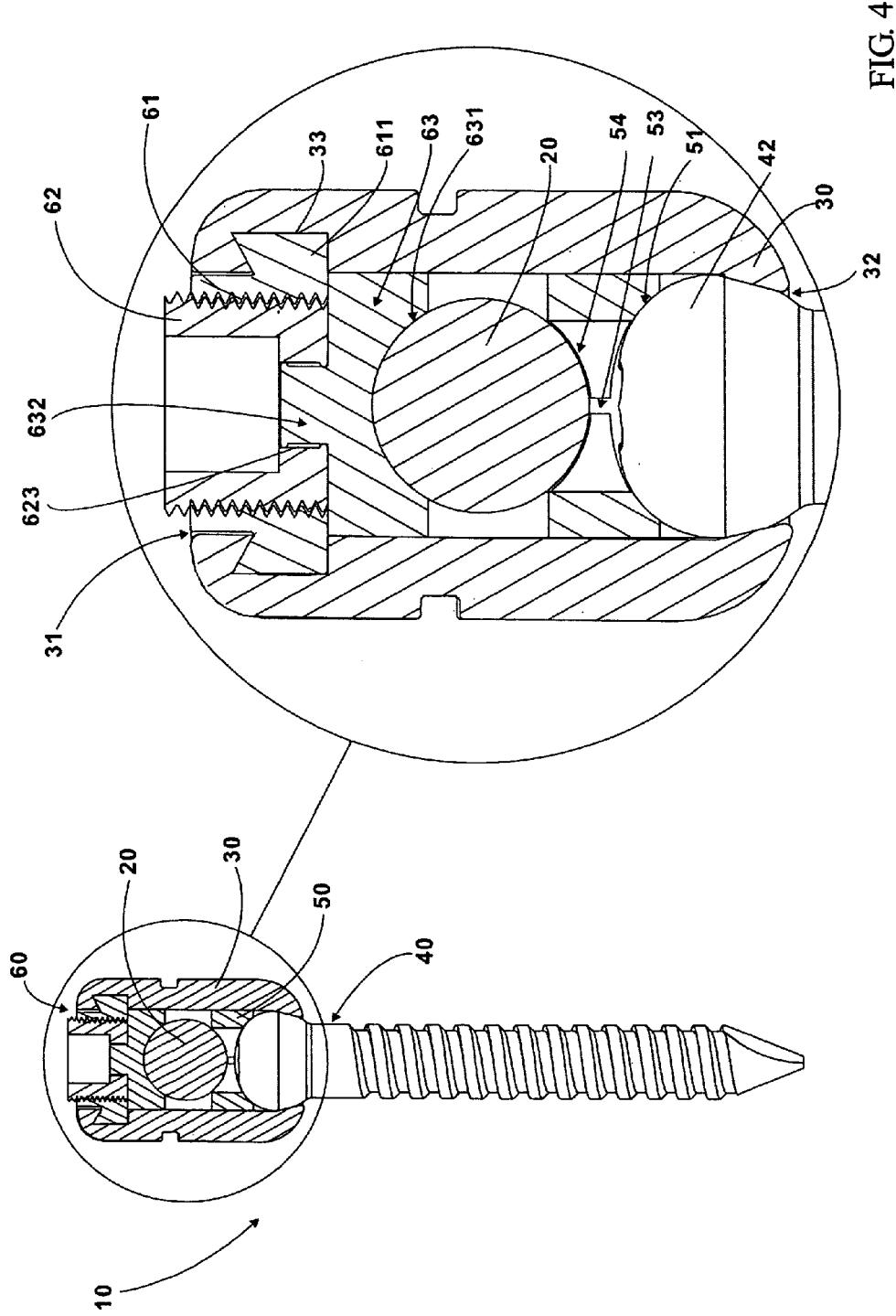
FIG. 4 shows a sectional view of the first preferred embodiment of the present invention shown in FIG. 3.

As shown in FIG. 4, the retaining edges 611 of said rotary fixation element are provided with an inclined plane having a higher outer side and a lower inner side; and the retaining recesses 33 of said fixation seat 30 are provided with an inclined plane having a higher outer side and a lower inner side, wherein said rotary fixation element 61 is engaged with said fixation seat 30 such that said inclined planes of said rotary fixation element 61 and said fixation seat 30 are in contact with each other, and thus the two side walls of said receiving slot 31 of said fixation seat are held by the rotary fixation element 61.

What is claimed is:

1. A vertebral retrieval device comprising:
    a retrieval rod which is used to retrieve spinal segments under treatment;
    a fixation seat provided with a receiving slot for receiving the retrieval rod, said receiving slot being provided on two opposite side walls with a retaining recess, and in a bottom with a through hole;
    a fastening screw is provided with a spherical head made integrally therewith, wherein said spherical head is rotatably received in said fixation seat when said fastening screw is inserted into said through hole of said fixation seat;
    a C-shaped ring provided with a concave down surface on one side, said C-shaped ring being able to be elastically deformed, received in said fixation seat and retained in said fixation seat by an expansion force resulting from said deformation, while said concave down surface resting on the spherical head of said fastening screw and another side of said C-shaped ring being adapted to receive said retrieval rod;
    a fixation assembly comprising a rotary fixation element provided with a threaded through hole, and two retaining edges opposite to each other; a pressing element having a projection at one side and a groove at another side; and a pressing screw having a round hole adapted to receive said projection of said pressing element, wherein said rotary fixation element is engaged with said fixation seat such that the two retaining edges are retained in said retaining recesses of said fixation seat, said pressing screw is threadably engaged in said threaded through hole of said rotary fixation element, and the pressing element is able to be pressed against said retrieval rod by threading said pressing screw, when the groove of said pressing element rests on said retrieval rod and said projection of said pressing element is received in said round hole of said pressing screw.

2. The device as defined in claim 1, wherein said retaining recesses of said fixation seat are located in inner sides of the two side walls of said receiving slot; wherein said retaining edges of said rotary fixation element are located in outer edges of said rotary fixation element.

3. The device as defined in claim 2, wherein said retaining edges of said rotary fixation element are provided with an inclined plane having a higher outer side and a lower inner side; wherein said retaining recesses of said fixation seat are provided with an inclined plane having a higher outer side and a lower inner side, wherein said rotary fixation element is engaged with said fixation seat such that said inclined planes of said rotary fixation element and said fixation seat are in contact with each other, and thus the two side walls of said receiving slot of said fixation seat are prevented from departing from each other.

4. The device as defined in claim 1, wherein said C-shaped ring is provided with a groove on said another side thereof, and said groove of said C-shaped ring is adapted to receive said retrieval rod.

5. The device as defined in claim 1, wherein a tool hole is provided in said pressing screw for facilitating the threadable engagement with said rotary fixation element.

* * * * *